US010343357B2

(12) United States Patent
Van Dijk (10) Patent No.: US 10,343,357 B2
(45) Date of Patent: Jul. 9, 2019

(54) INSERT ASSEMBLY FOR MANUFACTURING INTRAOCULAR LENSES

(71) Applicant: INNOVALENS B.V., Eindhoven (NL)

(72) Inventor: Emerentius Maria Josephus Antonius Van Dijk, Eindhoven (NL)

(73) Assignee: INNOVALENS B.V., Eindhoven (NL)

( * ) Notice: Subject to any disclaimer, the term of this patent is extended or adjusted under 35 U.S.C. 154(b) by 511 days.

(21) Appl. No.: 14/908,900

(22) PCT Filed: Jul. 30, 2014

(86) PCT No.: PCT/NL2014/050529
§ 371 (c)(1),
(2) Date: Jan. 29, 2016

(87) PCT Pub. No.: WO2015/016711
PCT Pub. Date: Feb. 5, 2015

(65) Prior Publication Data
US 2016/0167325 A1 Jun. 16, 2016

(30) Foreign Application Priority Data

Jul. 30, 2013 (NL) ..................................... 2011239

(51) Int. Cl.
*B29D 11/00* (2006.01)
*B29C 45/36* (2006.01)
(Continued)

(52) U.S. Cl.
CPC .............. *B29D 11/023* (2013.01); *A61F 2/16* (2013.01); *B29C 33/12* (2013.01);
(Continued)

(58) Field of Classification Search
CPC ... B29D 11/023; B29D 11/0048; B29C 33/12; B29C 33/3842; A61F 2/16
See application file for complete search history.

(56) References Cited

U.S. PATENT DOCUMENTS

| 4,815,690 A | 3/1989 | Shepherd |
| 5,702,735 A | 12/1997 | Martin et al. |
(Continued)

FOREIGN PATENT DOCUMENTS

| CN | 1352595 A | 6/2002 |
| WO | WO 01/42001 A1 | 6/2001 |

*Primary Examiner* — Mathieu D Vargot
(74) *Attorney, Agent, or Firm* — Johnson & Johnson Surgical Vision, Inc.

(57) ABSTRACT

An insert assembly for the purpose of an injection mold for manufacturing a first casting mold half of a casting mold for manufacture of an ophthalmic device, wherein the insert assembly is receivable in an injection mold half of the injection mold and wherein the insert assembly includes an insert assembly end surface which bounds an injection mold cavity of the injection mold for forming a first casting mold half. The insert end surface is provided with at least one notch which forms a bounding structure cavity for forming a bounding structure which is an integral part of the first casting mold half to be formed with the injection mold and which, after placement of a second casting mold half on the first casting mold half, bounds at least one haptics cavity which links up with a lens cavity, wherein the haptics cavity is so configured that in use of the casting mold, after curing of monomeric material deposited in the casting mold, an intraocular lens is formed which comprises a lens and integrally formed-on haptics.

16 Claims, 10 Drawing Sheets

(51) Int. Cl.
- *B29C 33/12* (2006.01)
- *B29D 11/02* (2006.01)
- *A61F 2/16* (2006.01)
- *B29C 33/38* (2006.01)
- *B29L 11/00* (2006.01)
- *B29C 45/26* (2006.01)

(52) U.S. Cl.
CPC .......... *B29C 33/3842* (2013.01); *B29C 45/36* (2013.01); *B29D 11/0048* (2013.01); *A61F 2002/169* (2015.04); *B29C 45/2673* (2013.01); *B29L 2011/0008* (2013.01); *B29L 2011/0016* (2013.01)

(56) References Cited

U.S. PATENT DOCUMENTS

| | | |
|---|---|---|
| 6,391,230 B1 | 5/2002 | Sarbadhikari |
| 2003/0062640 A1 | 4/2003 | Ansell et al. |
| 2006/0145369 A1 | 7/2006 | Lawton et al. |
| 2011/0098808 A1 | 4/2011 | Kobayashi et al. |

INSERT ASSEMBLY FOR MANUFACTURING INTRAOCULAR LENSES

FIELD

The invention relates to an insert assembly for the purpose of an injection mold for manufacturing a first casting mold half of a casting mold for manufacture of an ophthalmic device, wherein the casting mold comprises the first casting mold half and a second casting mold half which in a condition of placed onto each other bound a lens cavity of the ophthalmic device.

The invention further relates to an injection mold provided with such an insert assembly.

The invention also relates to a method for manufacturing a casting mold for manufacture of an ophthalmic device, wherein the casting mold comprises the first casting mold half and a second casting mold half which in a condition placed onto each other bound a lens cavity of the ophthalmic device.

The invention further relates to a casting mold for manufacturing an ophthalmic device.

The invention also relates to a method for manufacturing an intraocular lens with the aid of the casting mold, and to an intraocular lens obtained with that method.

BACKGROUND

The manufacture of intraocular lenses provided with haptics has hitherto been labor intensive. Often, the starting point is a flat circular disk of transparent plastic of a high optical quality. The disk is clamped in the clamping head of a turning lathe and a first side is worked for forming a first optically accurately defined surface. Next, the disk is again clamped in the clamping head of a turning lathe and the opposite side is worked for forming a second optically accurate surface. Next, the thus worked disk is brought to a miller, where large parts of the circumferential parts of the disk are milled off, except for so-called haptics or loops. These are thin and/or slender and hence flexible parts which are integrally connected with a central lens part. The haptics ensure that the intraocular lens retains its proper position in the lens cavity of the eye. It will be clear that manufacturing intraocular lenses in this way is particularly labor intensive and hence also costly.

US2011/0098808 relates to an intraocular lens and a method of manufacturing such a lens. While in paragraph [0063] it is stated that in the embodiment shown the intraocular lens 10 is of one piece design, with the optical part 12 and the haptics 14 integrally formed, it is not disclosed in that publication by what method this integral construction is obtained. While a cast mold method is described in [0109] to [0112], that description does not disclose that an intraocular lens with formed-on haptics is obtained directly, without aftertreatment. It is well possible that during cast molding a product is formed with a central part that possesses the desired optical properties, and a disk-shaped ring surrounding the central part, whereby in a follow-up step the haptics are formed from this ring by milling Then, also, a one piece intraocular lens is obtained with an optical part and integrally formed-on haptics. The manner of forming the haptics is not the subject of US2011/0098808; US'808 is about providing microstructures on the surface of the lens to influence cell growth.

Reference is further made to US2006/0145369 and U.S. Pat. No. 5,702,735 in which injection molds are disclosed for manufacturing casting mold halves for the purpose of the manufacture of contact lenses. With these known injection molds, use is made of optical inserts.

The object of the invention is to alleviate the problems of manufacturing intraocular lenses, so that the cost price of intraocular lenses can be reduced.

SUMMARY

To that end, according to a first aspect, the invention provides an insert assembly for the purpose of an injection mold for manufacturing a first casting mold half of a casting mold for manufacture of an ophthalmic device, wherein the casting mold comprises the first casting mold half and a second casting mold half which in a condition placed onto each other bound a lens cavity, wherein the insert assembly is receivable in an injection mold half of the injection mold and wherein the insert assembly comprises:

- an insert assembly end surface which bounds an injection mold cavity of the injection mold for forming the first casting mold half and which extends substantially perpendicular to an axial centerline of the insert assembly;
- an outer part assembly which has an outer part assembly end surface which forms a part of the insert assembly end surface;
- an inner part which has an optically accurately defined end surface which in a mounted condition is substantially at the outer part assembly end surface and which forms a part of the insert assembly end surface;
- at least one notch in the insert assembly end surface, which forms a bounding structure cavity for forming a bounding structure which is an integral part of the first casting mold half to be formed with the injection mold, such that in a condition of the first and the second casting mold halves placed onto each other, the bounding structure abuts against the second casting mold half and bounds at least one haptics cavity which links up with the lens cavity, wherein the haptics cavity is so configured that in use of the casting mold, after curing of monomeric material deposited in the casting mold, an ophthalmic device in the implementation of an intraocular lens is formed which comprises a lens and integrally formed-on haptics.

According to a next aspect of the invention, an injection mold is provided, which comprises:

- a first injection mold half in which an insert assembly according to any one of claims 1-9 is received;
- a second injection mold half which is movable relative to the first injection mold half from a closed to an opened position and vice versa,
- a first injection mold cavity which is formed in the closed condition of the injection mold, which is at least partly bounded by the first insert assembly, and which is configured for manufacturing the first casting mold half.

Further, the invention provides a method for manufacturing a casting mold for manufacture of an ophthalmic device, wherein the casting mold comprises a first casting mold half and a second casting mold half which in a condition placed onto each other bound a lens cavity, wherein the method either comprises:

- providing an injection mold according to claim 10 and providing a second injection mold comprising:
  - a second insert assembly provided with an optically accurately defined surface;
  - a second injection mold cavity which is formed in the closed condition of the injection mold, which is at least partly bounded by the optically accurately defined surface of the second insert assembly, and which is configured for manufacturing the second casting mold half;

or wherein the method comprises:

providing an injection mold according to claim 11;

wherein the method further comprises:

injection molding of the first casting mold half with an optically accurately defined surface part; and injection molding of the second casting mold half with an optically accurately defined surface part;

wherein in a condition of the first and the second casting mold halves placed onto each other, the bounding structure of the first casting mold half abuts against the second casting mold half and bounds at least one haptics cavity which links up with the lens cavity, wherein the haptics cavity is so configured that in use of the casting mold, after curing of monomeric material deposited in the casting mold, an ophthalmic device in the implementation of an intraocular lens is formed which comprises a lens and integrally formed-on haptics.

Further, the invention provides a casting mold for manufacturing an ophthalmic device, provided with:

a first casting mold half with an optically accurately defined surface part;

a second casting mold half with an optically accurately defined surface part;

wherein the first casting mold half and the second casting mold half in a condition placed onto each other bound a lens cavity, which lens cavity is at least partly bounded by the optically accurately defined surface parts;

wherein the casting mold is provided with:

a bounding structure which is an integral part of the first casting mold half, such that in a condition of the first and the second casting mold halves placed onto each other, the bounding structure abuts against the second casting mold half and bounds at least one haptics cavity which links up with the lens cavity, wherein the haptics cavity is so configured that in use of the casting mold, after curing of monomeric material deposited in the casting mold, an ophthalmic device in the implementation of an intraocular lens is formed which comprises a lens and integrally formed-on haptics.

The invention further provides a method for manufacturing an intraocular lens, wherein the method comprises:

providing a casting mold according to any one of claims 13-15 with the aid of the method according to claim 12;

injecting an amount of monomeric material into the first casting mold half;

placing the second casting mold half on the first casting mold half;

curing of the monomeric material that is in the casting mold for forming in the casting mold an intraocular lens which comprises a lens and integrally formed-on haptics.

Finally, the invention provides an intraocular lens obtained with the above-described method, i.e., the method according to claim 16.

With the aid of the insert assembly according to the invention, an injection mold according to the invention can be provided, with which, using the method according to the invention, a first casting mold half according to the invention can be manufactured. With the same injection mold or with another injection mold, a second casting mold half can be manufactured, whereby through combination of the first and the second casting mold halves a casting mold according to the invention is obtained. Owing to the particular construction of the insert assembly, a casting mold is obtained which is characterized by a bounding structure which is an integral part of the first casting mold half, such that in a condition of the first and the second casting mold halves placed onto each other, the bounding structure abuts against the second casting mold half and bounds at least one haptics cavity which links up with the lens cavity, the haptics cavity being so configured that in use of the casting mold, after curing of monomeric material deposited in the casting mold, an ophthalmic device in the implementation of an intraocular lens is formed which comprises a lens and integrally formed-on haptics.

In the making of an intraocular lens with haptics, therefore, the starting point is no longer a plastic disk which is formed into an intraocular lens by turning and milling operations with all associated costs of labor and material loss. Instead, a small amount of monomeric material is deposited in the first casting mold half and, by placement of the second casting mold half onto the first casting mold half, a casting mold cavity is formed which comprises both the lens cavity and the haptics cavities. After curing of monomeric material, an intraocular lens is obtained which is directly, or practically directly, suitable for placement in a lens cavity.

Further elaborations of the invention are described in the subclaims and will hereinafter be further clarified, with reference to the drawings, on the basis of an exemplary embodiment.

DETAILED DESCRIPTION

FIGS. 1-11 show in various views and cross sections an example of an insert assembly in which various embodiments of the invention are embodied. The various embodiments will be described hereinafter with reference to the figures. It is clear that the reference numerals in the following detailed description serve for clarification only and that the exemplary embodiments described are not limited to the example shown in the figures. Moreover, the various embodiments to be discussed hereinafter can be used independently of each other but can also be used in combinations of two or more embodiments with each other.

In the most general terms, an insert assembly 10 (see FIGS. 1-11) for the purpose of an injection mold 100 (see FIGS. 12-14) for manufacturing a first casting mold half 202 of a casting mold 200 (see FIGS. 15-17) for manufacturing an ophthalmic device (FIG. 18) is provided. The casting mold 200 comprises the first casting mold half 202 and a second casting mold half 204 which in a condition placed onto each other bound a lens cavity 206. The insert assembly 10 is receivable in an injection mold half 102 of the injection mold 100. The insert assembly 10 comprises an insert assembly end surface 14, 18, 22, 26 (see FIG. 1), which bounds an injection mold cavity 106 (see FIG. 13) of the injection mold 100 for forming the first casting mold half 202 and which extends substantially perpendicular to an axial centerline L of the insert assembly 10. Further, the insert assembly 10 comprises an outer part assembly 12, 16, 24 which has an outer part assembly end surface 14, 18, 26 which forms a part of the insert assembly end surface 14, 18, 22, 26. The insert assembly 10 also comprises an inner part 20 which has an optically accurately defined end surface 22 which in a mounted condition is situated substantially at the outer part assembly end surface 14, 18, 26 and which forms a part of the insert assembly end surface 14, 18, 22, 26. In the insert assembly end surface 14, 18, 22, 26, at least one notch 40, 42 is present which forms a bounding structure cavity for forming a bounding structure 208, 210 which is an integral part of the first casting mold half 202 to be formed with the injection mold 100. The bounding structure 208, 210 is designed such that in a condition of the first and the second casting mold halves 202, 204 placed onto each other, the bounding structure 208, 210 abuts against the second casting mold half 204 and bounds at least one haptics cavity 212 which links up with the lens cavity 206. The haptics cavity 212 is configured such that in use of the casting mold 200, after curing of monomeric material deposited in the casting mold 200, an ophthalmic device in the implementation of an intraocular lens 300 is formed which comprises a lens 302 and integrally formed-on haptics 304.

In an embodiment, the notch 40 can form at least one closed contour which surrounds the optically accurately defined end surface 22. The contour may then be so shaped as to form in the casting mold 200 a bounding structure 208 which comprises an upwardly projecting ridge which extends according to a corresponding closed contour and which in a condition of the first and the second casting mold halves 202, 204 placed one onto the other, abuts against the second casting mold half 204 and bounds the lens cavity 206 and the at least one haptics cavity 212.

In an embodiment, the at least one notch 40, 42 may be so shaped as to form in the first casting mold half 202 a bounding structure 208, 210 which comprises at least one upwardly projecting ridge 208, 210, the upwardly projecting ridge 208, 210 in cross section having a triangular shape with a sharp top. This triangular shape with sharp top is clearly visualized in FIGS. 10 and 11. Owing to the sharp top, upon placing the second casting mold half 204 on the first casting mold half 202, the monomeric material present in the first casting mold half that is in the haptics cavity 212 and the lens cavity 206 is effectively separated from the monomeric material that is present outside thereof. This is because the top, sharp in cross section, of the upwardly projecting ridges is, upon closure, pressed against the second casting mold half 204, such that adjacent the contact between the sharp top of the upwardly projecting ridge 208, 210 and the second casting mold half 204, the monomeric material is pressed away, and there a sharp separation is created between the monomeric material that is present in the haptics cavities 212 and the lens cavity 206, and the monomeric material that is present outside thereof. Owing to this sharp separation, there is directly obtained an intraocular lens with haptics that does not require any aftertreatment for the removal of flashes. After hydration, the intraocular lens is directly suitable for placement in an eye.

In an embodiment, the outer part assembly 12, 16, 24 can comprise an outer part 12 which may be provided with a central outer part passage 28. The outer part 12 has an end surface 14 which is part of the outer part assembly end surface 14, 18, 26. The outer part passage 28 forms an outer part passage opening in the end surface 14 of the outer part 12. The outer part passage opening is bounded by outer part passage edges (see FIG. 3). Further, the outer part assembly can comprise an intermediate part 16 which in the direction of the axial centerline L is slidably and fittingly received in the outer part passage 28. The intermediate part 16 has an intermediate part end surface 18 which is part of the outer part assembly end surface 14, 18, 26. The intermediate part end surface 18 is bounded by intermediate part circumferential edges 48 (see FIG. 2). The outer part passage edges 30 and/or the intermediate part circumferential edges 48 may be chamfered, such that a notch 40 triangular in cross section is obtained when the intermediate part 16 is placed in the outer part 12. The triangular notch 40 can form the at least one upwardly projecting ridge 208 of the first casting mold half 202.

The intermediate part 16 can be formed from the outer part 12 using wire sparking, Thus, in a single processing operation an intermediate part 16 with a complex outer circumference contour and an outer part passage 28 with a corresponding inner circumference contour can be formed. The chamfer of the outer part passage edges 30 may be effected, for instance, by means of a milling operation with a cone-shaped mill which rotates about the centerline of the cone. Similarly, also the intermediate part circumferential edges 48 of the intermediate part 16 could be chamfered. In a first variant, only the outer part passage edges 30 may be chamfered. In a second variant, only the intermediate part circumferential edges 48 may be chamfered, and in a third variant both the outer part passage edges 30 and the intermediate part circumferential edges 48 may be chamfered. Forming in this manner the intermediate part 16 the chamfered outer part edges 30 and/or the chamfered intermediate part circumferential edges 48 results in triangular notches 40 with a particularly sharp top, which minimizes the necessity for post-treating the intraocular lens 300 after removal from the casting mold.

In an embodiment, the intermediate part 16 may be provided with a central intermediate part passage 46 in which the inner part 20 is axially slidably and fittingly receivable.

In a further elaboration of the embodiment with the intermediate part 16, the intermediate part 16 of the insert assembly may be provided with at least one additional intermediate part passage 50. The at least one additional intermediate part passage 50 forms an intermediate part passage opening in the end surface 18 of the intermediate part 16, which intermediate part passage opening is bounded by intermediate part passage edges 52. The insert assembly 10 may then be provided with at least one intermediate part sub-element 24, associated with the at least one intermediate part passage 50, which is slidable in the direction of the axial centerline and thus, fittingly, receivable in the associated intermediate part passage 50. The intermediate sub-element 24 has an end surface 26 which is part of the outer part assembly end surface 14, 18, 22, 26. The end surface 26 of the intermediate part sub-element 24 is bounded by intermediate part sub-element circumferential edges 32. The intermediate part passage edges 52 and/or the intermediate part sub-element circumferential edges 32 are chamfered in such an embodiment, such that a notch 42 triangular in cross section (see FIG. 11) is obtained when the intermediate part sub-element 24 is placed in the intermediate part 16. This triangular notch 42 forms an additional upwardly projecting ridge 210 of the first casting mold half 202 for bounding a portion of the haptics cavity 212.

Figure 18:
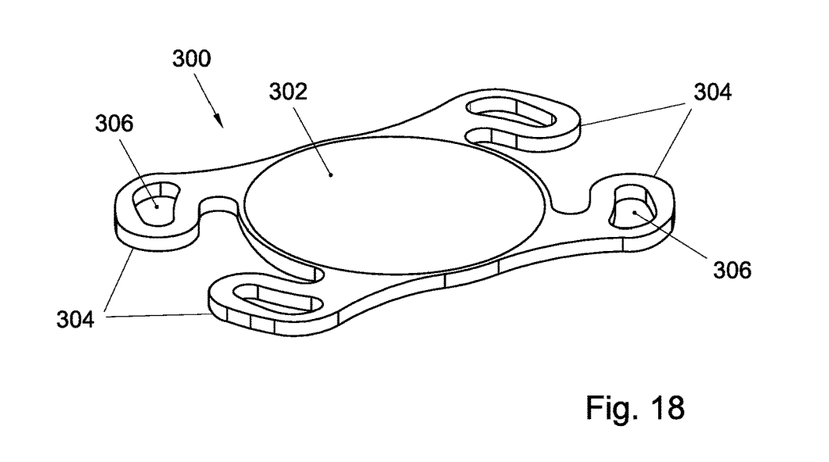
FIG. 18 shows a perspective view of an exemplary embodiment of an intraocular lens provided with formed-on haptics, which is manufactured using the two casting mold halves of FIGS. 15 and 16.

With such sub-elements, for instance, openings 306 can be formed in the haptics 304 of the intraocular lens as is visible in the example of FIG. 18. Such haptics 304 with openings are also referred to in practice as loops. Also the intermediate part sub-elements 24 can be formed by wire sparking from the intermediate part 16. The chamfer of the intermediate part sub-element circumferential edges 32 and/or the intermediate part passage edges 52 can be effected with a milling operation by a cone-shaped mill. Thus, triangular notches 42 are obtained with a very sharp top. For this aspect, too, it holds that with a notch 42 with such a very sharp top, upwardly projecting ridges 210 are formed in the first casting mold half 202 with a particularly sharp top. Owing to thus implemented upwardly projecting ridges, the necessity for post-treating the intraocular lens 300 which is obtained with the casting mold 200 is minimized because the chance of formation of flashes is minimized.

Figure 1:
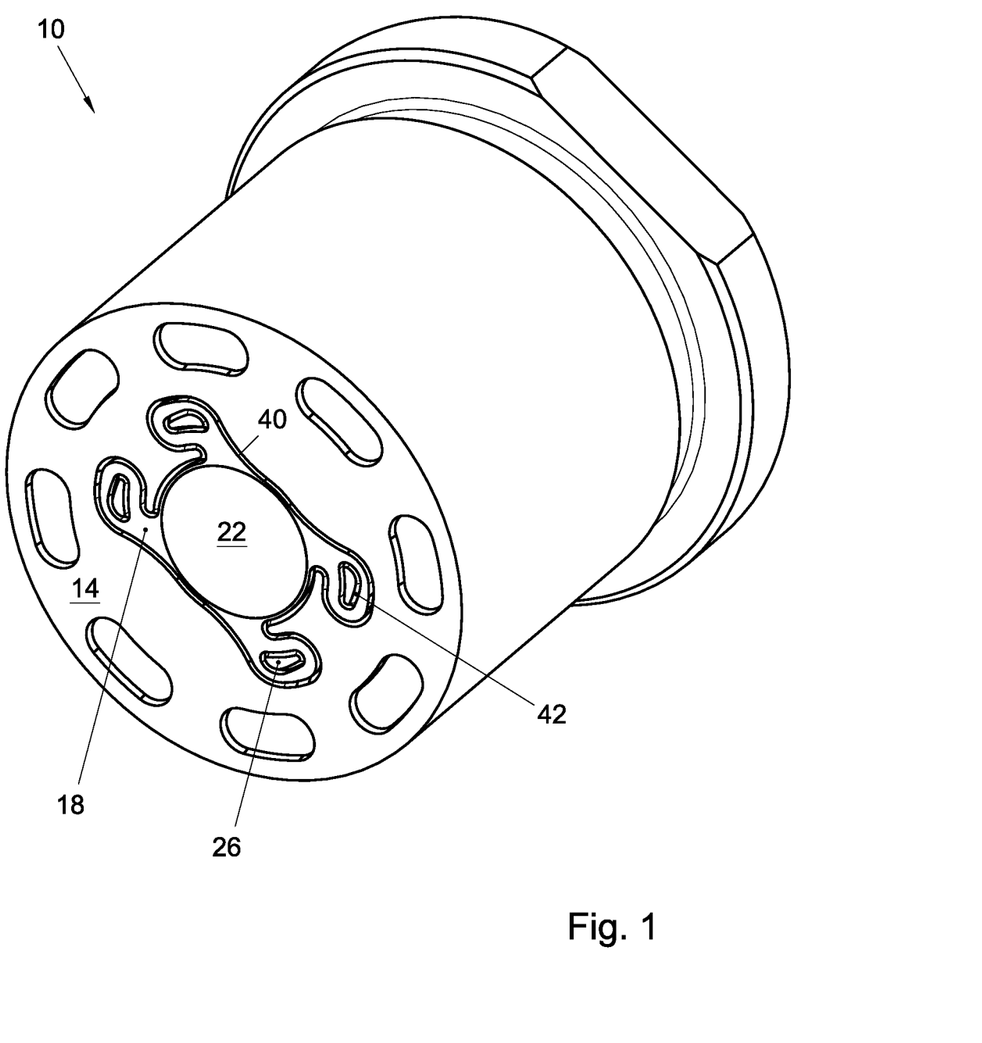
FIG. 1 shows a perspective view of an exemplary embodiment of the insert assembly.
Figure 2:
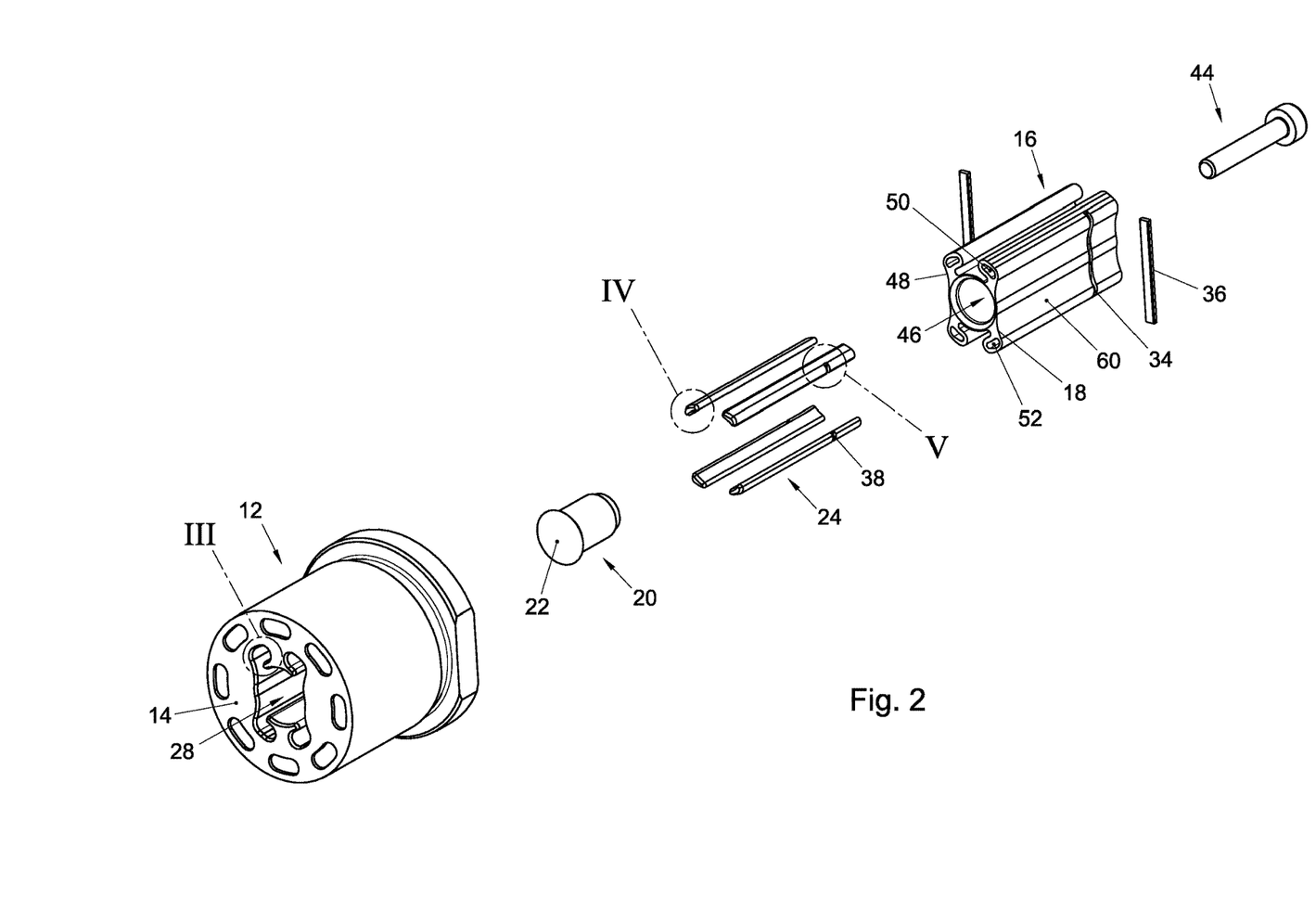
FIG. 2 shows an exploded view of the exemplary embodiment represented in FIG. 1 in a similar perspective view.
Figure 3:
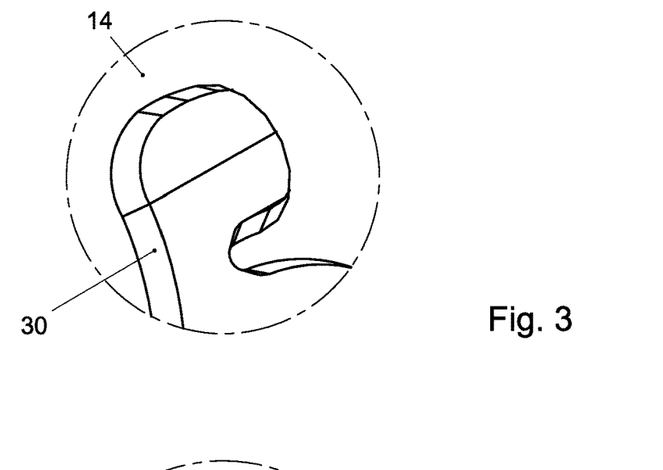
FIG. 3 shows detail III of FIG. 2.
Figure 4:
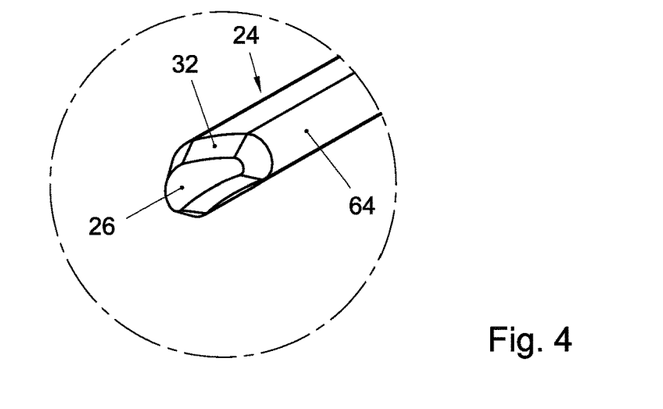
FIG. 4 shows detail IV of FIG. 2.
Figure 5:
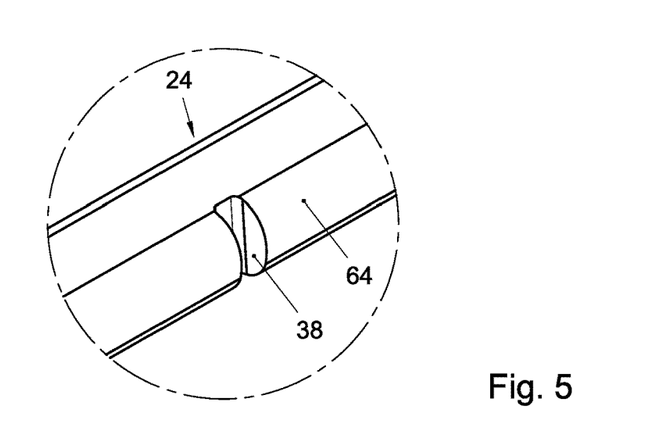
FIG. 5 shows detail V of FIG. 2.
Figure 6:
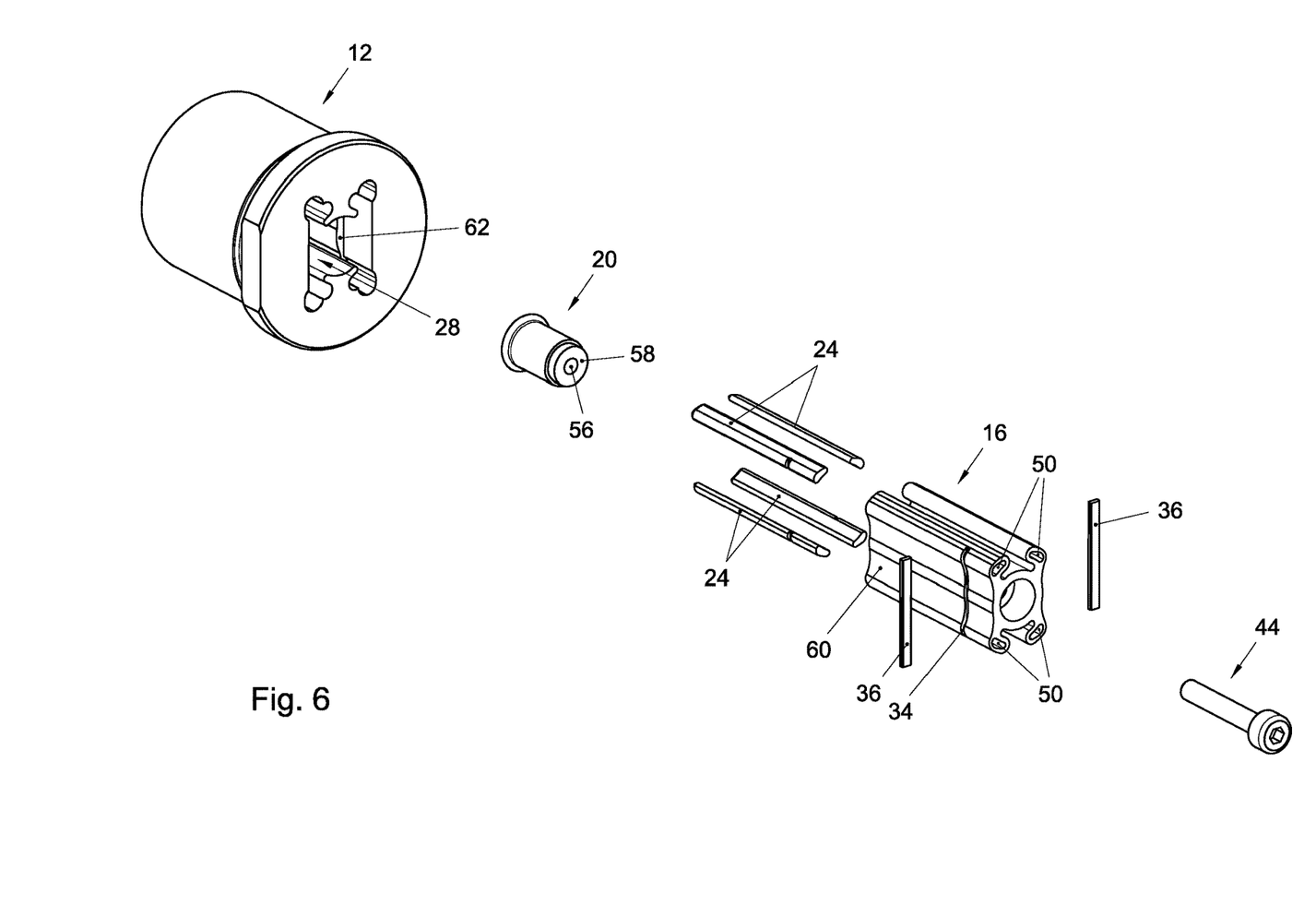
FIG. 6 shows an exploded view of the exemplary embodiment represented in FIG. 1 in a different perspective view.
Figure 7:
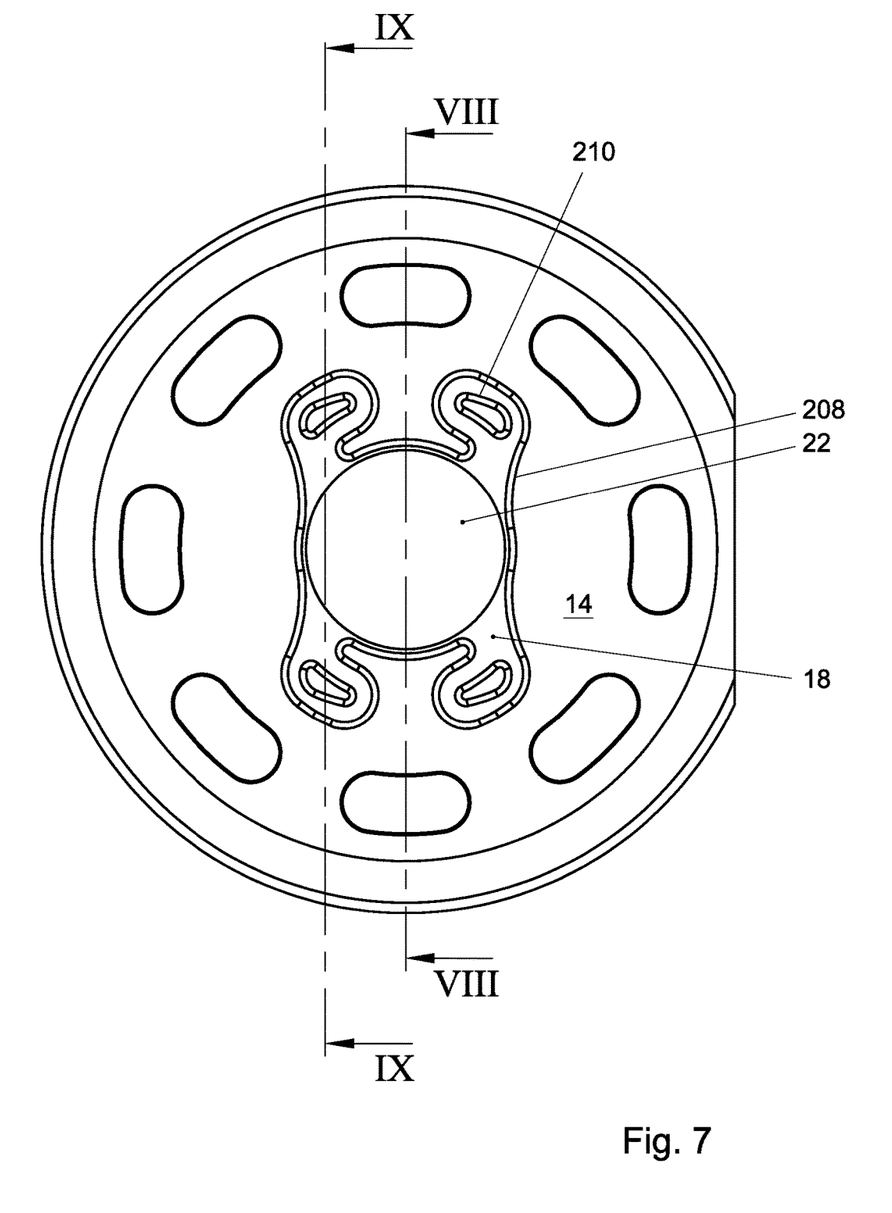
FIG. 7 shows a front view of the insert assembly end surface.
Figure 8:
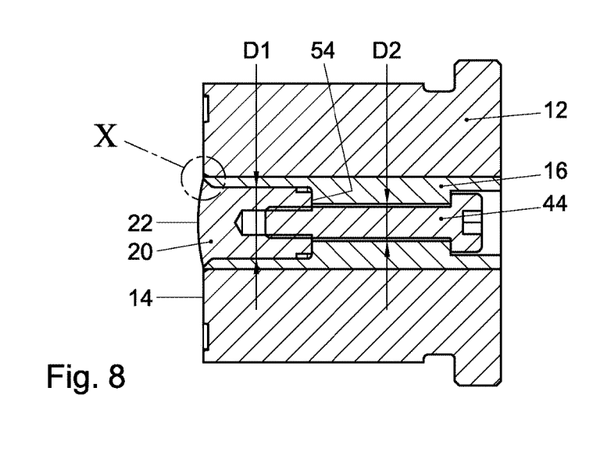
FIG. 8 shows a cross sectional view along line VIII-VIII of FIG. 7.
Figure 9:
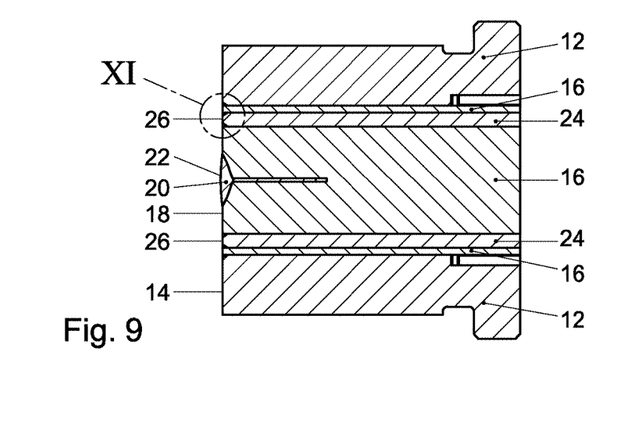
FIG. 9 shows a cross sectional view along line IX-IX of FIG. 7.
Figure 10:
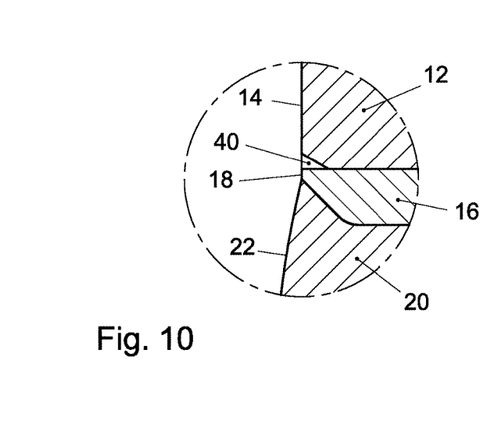
FIG. 10 shows detail X of FIG. 8.
Figure 11:
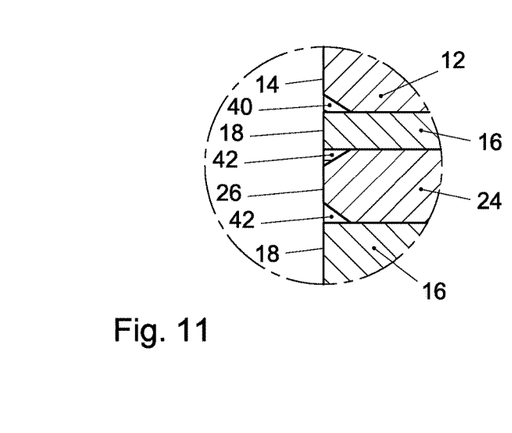
FIG. 11 shows detail XI of FIG. 9.

In an embodiment, of which an example is shown in FIG. 8, the central intermediate part passage 46, viewed from the intermediate part end surface 18, can, over a first length part of the intermediate part passage 46, have a first diameter D1 and over a second length part that links up with the first length part have a second diameter D2 that is smaller than the first diameter D1. At the transition from the first to the second length part, a stop surface 54 may be formed which extends substantially perpendicular to the axial centerline L. The inner part 20 may be provided, at the end opposite the optically accurately defined end surface, with a second end surface 58 in which a bore 56 is provided with internal thread. The insert assembly 10 may then be provided with a bolt 44 which is configured for engagement of the internal thread of the bore 56 and with the aid of which the inner part 20 is detachably mountable in the intermediate part 16. In the mounted condition of the inner part 20 in the intermediate part 16, the second end surface 58 can have the bore abutting against the stop surface 54. Thus, an accurate positioning of the inner part 20 in the intermediate part 16 in axial direction can be realized.

In an embodiment, of which an example is shown in FIGS. 2-6, the insert assembly may be provided with at least one keyway 34 which is provided in an intermediate part circumferential wall 60 extending in axial direction of the intermediate part 16. The at least one keyway 34 can extend substantially perpendicular to the axial centerline L. Further, in the outer part passage 28 a stop surface 62 may be provided. The stop surface 62 is preferably remote from the insert assembly end surface 14, 18, 22, 26. In such an embodiment, the insert assembly 10 may further be provided with at least one key 36 which is fittingly receivable in the associated at least one keyway 34. In a mounted condition of the intermediate part 16 in the outer part 12, the at least one key 36 is received in the associated at least one keyway 34, the key 36 abuts against the stop surface 62 in the outer part passage 28, so that the intermediate part 16 is positioned in axial direction relative to the outer part 12.

In an embodiment, of which an example is shown in FIGS. 2-6, also each intermediate part sub-element 24 may be provided with a keyway 38 which is provided in an intermediate part sub-element circumferential wall 64 which extends parallel to the axial centerline L. This at least one keyway 38 extends substantially perpendicular to the axial centerline L. In a mounted condition of the insert assembly 10, the at least one key 36 is received in the keyway 34 of the intermediate part 16 and also in the keyway 38 of the intermediate part sub-element 24, and the at least one key abuts against the stop surface 62 in the outer part passage 28, so that both the intermediate part 16 and the at least one intermediate part sub-element 24 are positioned in axial direction relative to the outer part 12.

Figure 12:
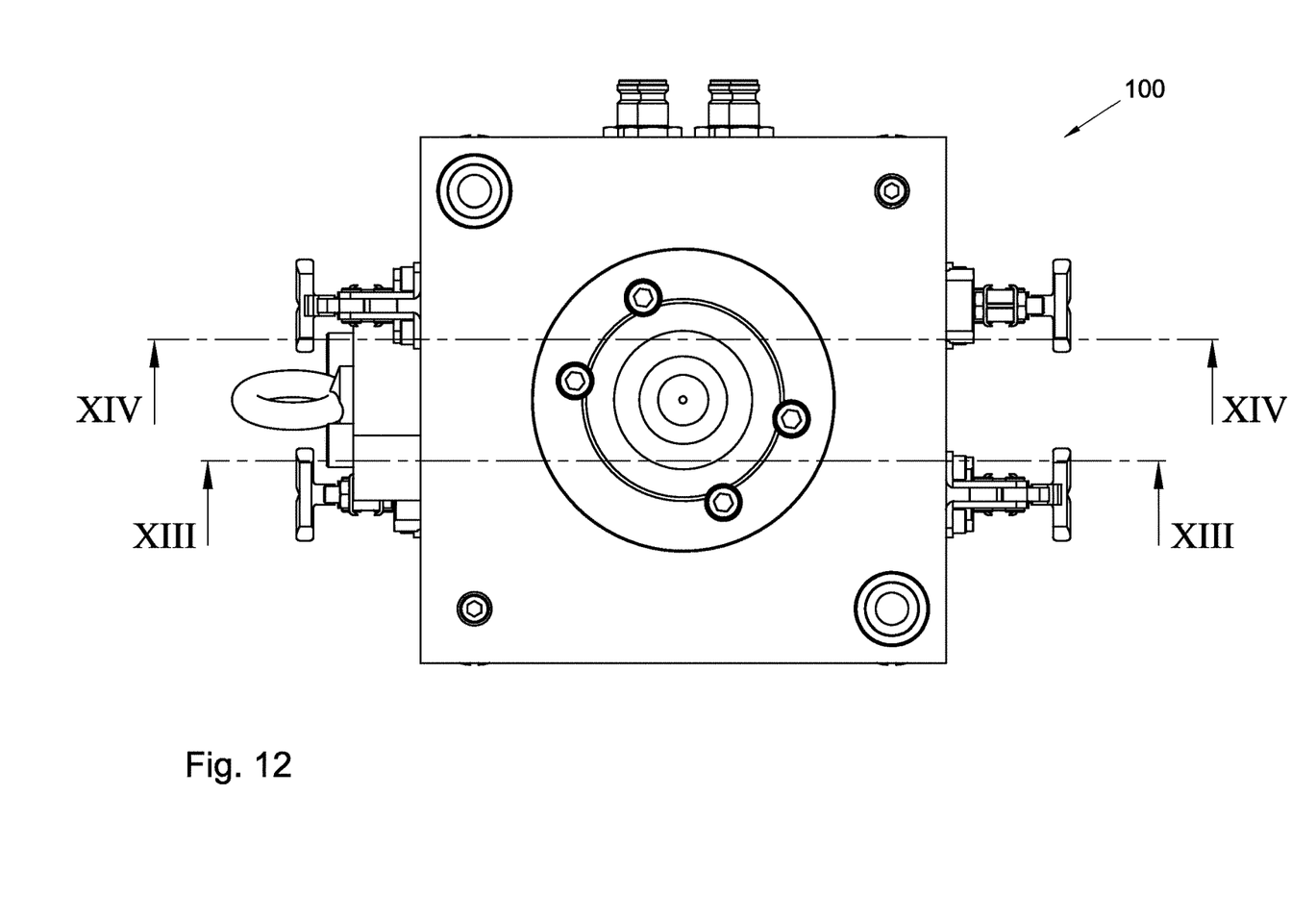
FIG. 12 shows a front view of an exemplary embodiment of an injection mold in which the exemplary embodiment of the first insert assembly is received for manufacturing a first casting mold half and in which also an exemplary embodiment of a second insert assembly is received for manufacturing a second casting mold half.
Figure 13:
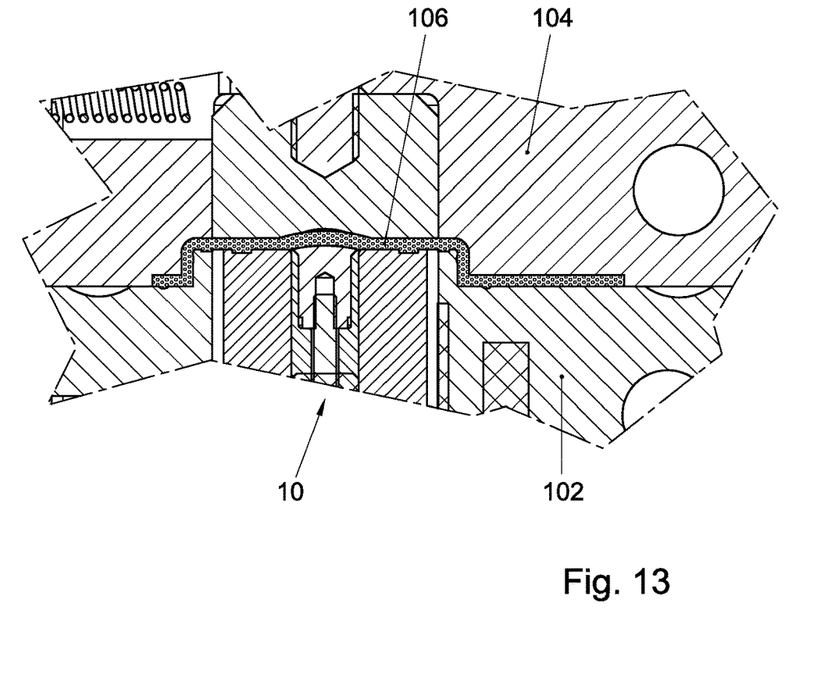
FIG. 13 shows a portion of a sectional view along line XIII-XIII of FIG. 12.
Figure 14:
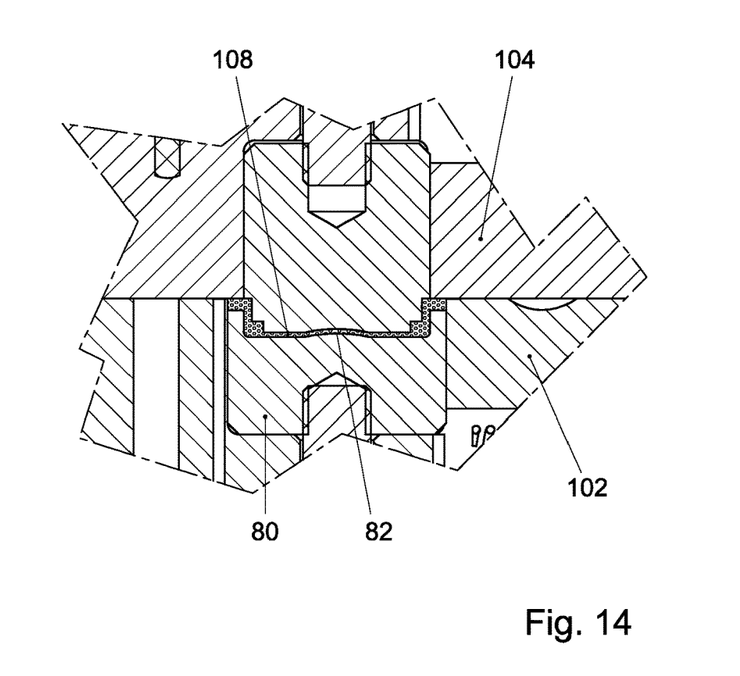
FIG. 14 shows a portion of a sectional view along line XIV-XIV of FIG. 12.

FIGS. 12-14 show an example of an embodiment of an injection mold 100 which comprises a first injection mold half 102 in which an insert assembly 10 according to the invention is received (see FIG. 13). Further, the injection mold 100 comprises a second injection mold half 104 which is movable relative to the first injection mold half 102 from a closed to an opened position and vice versa. The injection mold 100 in its closed condition forms a first injection mold cavity 106, which is at least partly bounded by the insert assembly end surface 14, 18, 22, 26 of the first insert assembly 10, and which is configured for manufacturing the first casting mold half 202.

In an embodiment, of which an example is shown in FIGS. 12-14, the injection mold 100 may further comprise a second insert assembly 80 (see FIG. 14) which is provided with an optically accurately defined surface 82. In such an embodiment, the injection mold 100 in a closed condition thereof further forms a second injection mold cavity 108. This second injection mold cavity 108 is at least partly bounded by the second insert assembly 80, and is configured for manufacturing the second casting mold half 204.

In an embodiment of the invention, further, a method for manufacturing a casting mold 200 for manufacture of an ophthalmic device is provided. The casting mold 200 comprises a first casting mold half 202 and a second casting mold half 204 which in a condition placed onto each other bound a lens cavity. The method comprises providing either an injection mold 100 provided with only insert assemblies 10 according to the invention and providing a second injection mold which is provided with a second insert assembly 80 provided with an optically accurately defined surface 82 and which in the closed condition of the injection mold forms a second injection mold cavity 108 which is at least partly bounded by the optically accurately defined surface 82 of the second insert assembly, and which is configured for manufacturing the second casting mold half 204. In an alternative embodiment of the method, the method can comprise providing an injection mold according to claim 11, so that with the same injection mold 100 both first casting mold halves 202 and second casting mold halves 204 can be manufactured. Further, the method comprises injection molding of the first casting mold half 202 with an optically accurately defined surface 214 and injection molding of the second casting mold half 204 with an optically accurately defined surface part 216. The injection mold 100 is then preferably so configured that the bounding structure 208, 210 of the first casting mold half 202, in a condition of the first and second casting mold halves 202, 204 placed onto each other, abuts against the second casting mold half 204 and bounds at least one haptics cavity 212 which links up with the lens cavity 206. The thus formed haptics cavity 212 is then so configured that in use of the casting mold 200, after curing of monomeric material deposited in the casting mold 200, an ophthalmic device implemented as an intraocular lens 300 is formed which comprises a lens 302 and integrally formed-on haptics 304.

Figure 15:
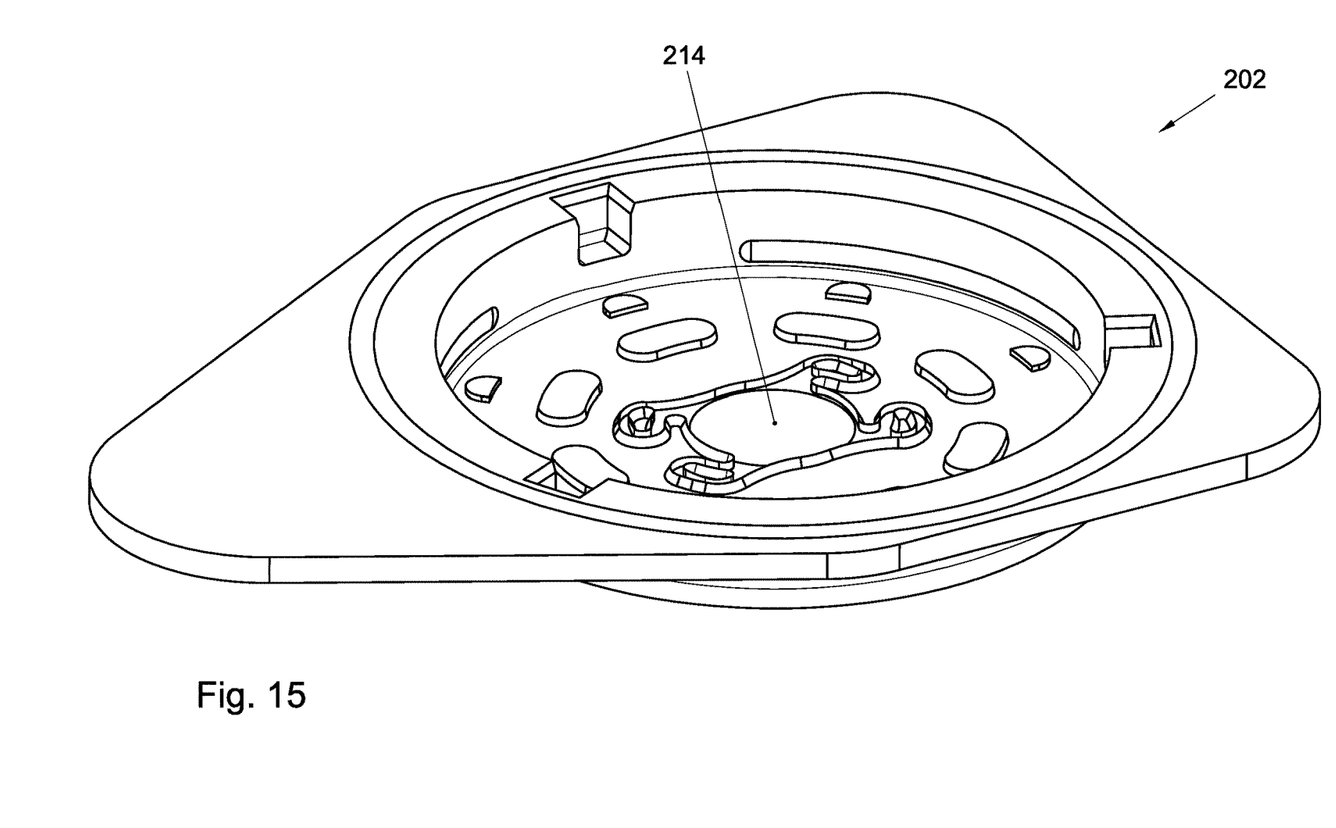
FIG. 15 shows a perspective view of an exemplary embodiment of the first casting mold half.
Figure 16:
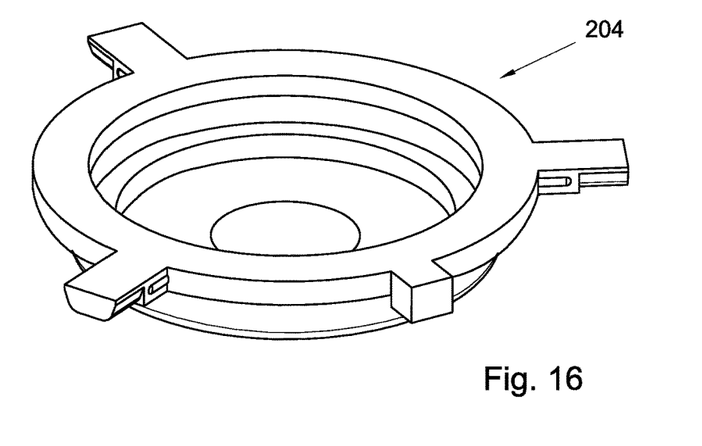
FIG. 16 shows a perspective view of an exemplary embodiment of the second casting mold half.
Figure 17:
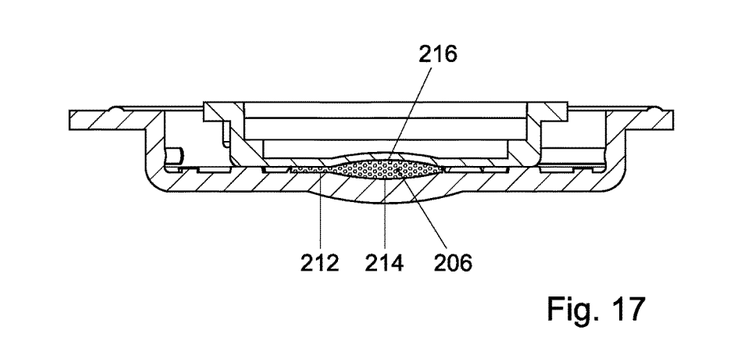
FIG. 17 shows a cross sectional view of a casting mold which is filled with monomeric material, the second casting mold half placed on the first casting mold half.

Further, a casting mold 200 is provided for manufacturing an ophthalmic device. An example of such a casting mold is shown in FIGS. 15-17. The casting mold 200 comprises a first casting mold half 202 with an optically accurately defined surface part 214 and a second casting mold half 204 with an optically accurately defined surface part 216. The first casting mold half 202 and the second casting mold half 204, in a condition placed onto each other, bound a lens cavity 206. The lens cavity 206 is at least partly bounded by the above-mentioned optically accurately defined surface parts 214, 216. The casting mold 200 is characterized by a bounding structure 208, 210 which is an integral part of the first casting mold half 202 and which is so configured that in a condition of the first and the second casting mold halves 202, 204 placed onto each other, the bounding structure 208, 210 abuts against the second casting mold half 204 and bounds at least one haptics cavity 212 which links up with the lens cavity 206. The haptics cavity 212 is so configured that in use of the casting mold 200, after curing of monomeric material deposited in the casting mold 200, an ophthalmic device in the implementation of an intraocular lens 300 is formed which comprises a lens 302 and integrally formed-on haptics 304.

Such an intraocular lens 300 can, after hydration, be directly ready for use.

In an embodiment, of which an example is shown in FIGS. 15-17, the bounding structure can comprise an upwardly projecting ridge which extends according to a closed contour and which, in a condition of the first and the second casting mold halves 202, 204 placed onto each other, abuts against the second casting mold half 204 and bounds the lens cavity 206 and the at least one haptics cavity 212.

In an embodiment, the at least one upwardly projecting ridge 208, 210 can have in cross section a triangular shape with a sharp top. As already indicated hereinabove, by virtue of the sharp top, upon placement of the second casting mold half 204 on the first casting mold half 202, the monomeric material in the first casting mold half that is present in the haptics cavity 212 and the lens cavity 206 is effectively separated from the monomeric material that is present outside thereof. This is because the cross-sectionally sharp tops of the upwardly projecting ridges 208, 210 are, upon closure, pressed against the second casting mold half 204, such that at the location of the contact between the sharp top of the upwardly projecting ridge 208, 210 and the second casting mold half 204, the monomeric material is pressed away and there a sharp separation is created between the monomeric material that is in the haptics cavities 212 and the lens cavity 206 and the monomeric material that is present outside thereof. As a result, an intraocular lens 300 is formed without flashes, so that a post-treatment of the intraocular lens 300, for instance for removing flashes, can be omitted.

Further, a method is provided for manufacturing an intraocular lens. The method comprises providing a casting mold 200 according to any one of claims 13-15 with the help of the method according to claim 12. Further, the method comprises:

injecting an amount of monomeric material into the first casting mold half 202;

placing the second casting mold half 204 on the first casting mold half 202;

curing the monomeric material that is in the casting mold 200 for forming in the casting mold 200 an intraocular lens 300 which comprises a lens 302 and integrally formed-on haptics 304.

After carrying out the method, the intraocular lens 300 can undergo a hydration treatment so that it softens and the lens 300 can be packaged in a package in which it is immersed in a fluid. The package could be formed by the first casting mold half 202 which is covered with a foil. However, alternative packages are also possible. It is known to package intraocular lenses in a special holder which is immersed in a fluid that is in a bottle. The holder can be simply mounted in an injection device with the aid of which the intraocular lens 300 can be injected into the eye.

The invention further provides an intraocular lens 300 which has been obtained with the above-described method.

While the invention has been represented and described in detail with reference to the drawings, the drawings and description should be construed by way of example only. The invention is not limited to the embodiments described. Features described in dependent claims may be combined with each other. The reference numerals in the claims and the description of the drawings must not be construed as limitations of the embodiments to just the examples shown in the drawings, but serve for clarification only. Different combinations of embodiments are possible.

In an alternative embodiment, the notches 40, 42 could also be formed in a manner other than by wire sparking and milling. While such manner of forming the notches 40, 42 is preferred because it allows notches with a very sharp top to be obtained, currently, with laser engraving techniques notches in a metal surface can also be formed with a sharp top in the deepest range. Such tops, however, will always have a certain rounding Accordingly, the casting mold will then have upwardly projecting ridges that have a slightly rounded top. The chance of flashes forming in a thus formed casting mold during the molding of an intraocular lens therein is therefore somewhat greater but may yet be acceptable in practice.

The invention claimed is:

1. An insert assembly for the purpose of an injection mold for manufacturing a first casting mold half of a casting mold for manufacture of an ophthalmic device, wherein the casting mold comprises the first casting mold half and a second casting mold half which in a condition placed onto each other bound a lens cavity, wherein the insert assembly is receivable in an injection mold half of the injection mold and wherein the insert assembly comprises:

an insert assembly end surface, which bounds an injection mold cavity of the injection mold for forming the first casting mold half and which extends substantially perpendicular to an axial centerline of the insert assembly;

an outer part assembly which has an outer part assembly end surface which forms a part of the insert assembly end surface;

an inner part which has an optically accurately defined end surface which in a mounted condition is substantially adjacent the outer part assembly end surface and which forms a part of the insert assembly end surface; and at least one notch in the insert assembly end surface which forms a bounding structure cavity for forming a bounding structure which is an integral part of the first casting mold half to be formed with the injection mold, such that, in a condition of the first and the second casting mold halves placed onto each other, the bounding structure abuts against the second casting mold half and bounds at least one haptics cavity which links up with the lens cavity, wherein the haptics cavity is so configured that in use of the casting mold, after curing of monomeric material deposited in the casting mold, an ophthalmic device in the implementation of an intraocular lens is formed which comprises a lens and integrally formed-on haptics.

2. The insert assembly according to claim 1, wherein the notch forms at least one closed contour that surrounds the optically accurately defined surface, wherein the contour is so shaped as to form in the casting mold a bounding structure which comprises an upwardly projecting ridge which extends according to a corresponding closed contour and which, in a condition of the first and the second casting mold halves placed onto each other, abuts against the second casting mold half and bounds the lens cavity and the at least one haptics cavity.

3. The insert assembly according to claim 1, wherein the at least one notch is so shaped as to form in the first casting mold half a bounding structure which comprises at least one upwardly projecting ridge, wherein the upwardly projecting ridge in cross section has a triangular shape with a sharp top.

4. The insert assembly according to claim 3, wherein the outer part assembly comprises:

an outer part provided with a central outer part passage, wherein the outer part has an end surface which is part of the outer part assembly end surface, wherein the outer part passage forms an outer part passage opening in the end surface of the outer part, which is bounded by outer part passage edges; and an intermediate part which in the direction of the axial centerline is slidably and fittingly received in the outer part passage, wherein the intermediate part has an intermediate part end surface which is part of the outer part assembly end surface, wherein the intermediate part end surface is bounded by intermediate part circumferential edges, wherein the outer part passage edges and/or the intermediate part circumferential edges are chamfered, such that a notch triangular in cross section is obtained when the intermediate part is placed in the outer part, which triangular notch forms the at least one upwardly projecting ridge of the first casting mold half.

5. The insert assembly according to claim 4, wherein the intermediate part is provided with:

a central intermediate part passage in which the inner part is axially slidably and fittingly receivable.

6. The insert assembly according to claim 4, wherein the intermediate part is provided with:

at least one additional intermediate part passage, wherein the at least one additional intermediate part passage forms an intermediate part passage opening in the end surface of the intermediate part which is bounded by intermediate part passage edges; and wherein the insert assembly comprises:

at least one intermediate part sub-element, associated with the at least one intermediate part passage, which in the direction of the axial centerline is slidably and fittingly receivable in the associated intermediate part passage, wherein the intermediate part sub-element has an end surface which is part of the outer part assembly end surface, wherein the end surface of the intermediate part sub-element is bounded by intermediate part sub-element circumferential edges, wherein the intermediate part passage edges and/or the intermediate part sub-element circumferential edges are chamfered, such that a notch triangular in cross section is obtained when the intermediate part sub-element is placed in the intermediate part, which triangular notch forms an additional upwardly projecting ridge of the first casting mold half for bounding a portion of the haptics cavity.

7. The insert assembly according to claim 5, wherein the central intermediate part passage, viewed from the intermediate part end surface, over a first length part of the intermediate part passage has a first diameter and over a second length part that links up with the first length part is provided with a second diameter which is smaller than the first diameter, wherein at the transition from the first to the second length part a stop surface is formed which extends substantially perpendicular to the axial centerline, wherein the inner part at the end opposite the optically accurately defined end surface is provided with a second end surface in which a bore is provided with internal thread, wherein the insert assembly is provided with a bolt which is configured for engagement of the internal thread of the bore and with the aid of which the inner part is detachably mountable in the intermediate part, wherein in the mounted condition of the inner part in the intermediate part the second end surface abuts by the bore against the stop surface.

8. The insert assembly according to claim 4, provided with:

at least one keyway which is provided in an intermediate part circumferential wall extending in axial direction of the intermediate part, wherein the at least one keyway extends substantially perpendicular to the axial centerline;

a stop surface which is arranged in the outer part passage, wherein the stop surface is remote from the insert assembly end surface; and at least one key which is fittingly receivable in the associated at least one keyway, wherein in a mounted condition of the intermediate part in the outer part, the at least one key is received in the associated at least one keyway and abuts against the stop surface in the outer part passage, so that the intermediate part is positioned in axial direction relative to the outer part.

9. The insert assembly according to claim 8, wherein the intermediate part is provided with:

at least one additional intermediate part passage, wherein the at least one additional intermediate part passage forms an intermediate part passage opening in the end surface of the intermediate part which is bounded by intermediate part passage edges; and wherein the insert assembly comprises:
at least one intermediate part sub-element, associated with the at least one intermediate part passage, which in the direction of the axial centerline is slidably and fittingly receivable in the associated intermediate part passage, wherein the intermediate part sub-element has an end surface which is part of the outer part assembly end surface, wherein the end surface of the intermediate part sub-element is bounded by intermediate part sub-element circumferential edges,
wherein the intermediate part passage edges and/or the intermediate part sub-element circumferential edges are chamfered, such that a notch triangular in cross section is obtained when the intermediate part sub-element is placed in the intermediate part, which triangular notch forms an additional upwardly projecting ridge of the first casting mold half for bounding a portion of the haptics cavity,
wherein each intermediate part sub-element is provided with a keyway which is provided in an intermediate part sub-element circumferential wall which extends parallel to the axial centerline, wherein the keyway extends substantially perpendicular to the axial centerline, wherein in a mounted condition of the insert assembly the at least one key is received in the keyway of the intermediate part and also in the keyway of the intermediate part sub-element and abuts against the stop surface in the outer part passage, so that both the intermediate part and the at least one intermediate part sub-element are positioned in axial direction relative to the outer part.

10. An injection mold comprising:
a first injection mold half in which an insert assembly is received, wherein the insert assembly comprises:
an insert assembly end surface, which bounds an injection mold cavity of the injection mold for forming the first casting mold half and which extends substantially perpendicular to an axial centerline of the insert assembly;
an outer part assembly which has an outer part assembly end surface which forms a part of the insert assembly end surface;
an inner part which has an optically accurately defined end surface which in a mounted condition is substantially adjacent the outer part assembly end surface and which forms a part of the insert assembly end surface; and
at least one notch in the insert assembly end surface which forms a bounding structure cavity for forming a bounding structure which is an integral part of the first casting mold half to be formed with the injection mold, such that, in a condition of the first and the second casting mold halves placed onto each other, the bounding structure abuts against the second casting mold half and bounds at least one haptics cavity which links up with the lens cavity, wherein the haptics cavity is so configured that in use of the casting mold, after curing of monomeric material deposited in the casting mold, an ophthalmic device in the implementation of an intraocular lens is formed which comprises a lens and integrally formed-on haptics;
a second injection mold half which is movable relative to the first injection mold half from a closed to an opened position and vice versa; and
a first injection mold cavity which is formed in the closed condition of the injection mold, which is at least partly bounded by the insert assembly end surface of the first insert assembly, and which is configured for manufacturing the first casting mold half.

11. The injection mold according to claim 10, further comprising:
a second insert assembly provided with an optically accurately defined surface; and
a second injection mold cavity which is formed in the closed condition of the injection mold, which is at least partly bounded by the second insert assembly, and which is configured for manufacturing the second casting mold half.

12. A method for manufacturing a casting mold for manufacture of an ophthalmic device, wherein the casting mold comprises a first casting mold half and a second casting mold half which in a condition placed onto each other bound a lens cavity, wherein the method comprises:
providing an injection mold comprising:
a first injection mold half in which an insert assembly is received, wherein the insert assembly comprises:
an insert assembly end surface, which bounds an injection mold cavity of the injection mold for forming the first casting mold half and which extends substantially perpendicular to an axial centerline of the insert assembly;
an outer part assembly which has an outer part assembly end surface which forms a part of the insert assembly end surface;
an inner part which has an optically accurately defined end surface which in a mounted condition is substantially adjacent the outer part assembly end surface and which forms a part of the insert assembly end surface; and
at least one notch in the insert assembly end surface which forms a bounding structure cavity for forming a bounding structure which is an integral part of the first casting mold half to be formed with the injection mold, such that, in a condition of the first and the second casting mold halves placed onto each other, the bounding structure abuts against the second casting mold half and bounds at least one haptics cavity which links up with the lens cavity, wherein the haptics cavity is so configured that in use of the casting mold, after curing of monomeric material deposited in the casting mold, an ophthalmic device in the implementation of an intraocular lens is formed which comprises a lens and integrally formed-on haptics;
a second injection mold half which is movable relative to the first injection mold half from a closed to an opened position and vice versa; and
a first injection mold cavity which is formed in the closed condition of the injection mold, which is at least partly bounded by the insert assembly end surface of the first insert assembly, and which is configured for manufacturing the first casting mold half; and
providing a second injection mold comprising:
a second insert assembly provided with an optically accurately defined surface; and
a second injection mold cavity which is formed in the closed condition of the injection mold, and which is at least partly bounded by the optically accurately defined surface of the second insert assembly, and which is configured for manufacturing the second casting mold half;

injection molding the first casting mold half with an optically accurately defined surface part; and injection molding the second casting mold half with an optically accurately defined surface part;

wherein in a condition of the first and the second casting mold halves placed onto each other, the bounding structure of the first casting mold half abuts against the second casting mold half and bounds at least one haptics cavity which links up with the lens cavity, wherein the haptics cavity is so configured that in use of the casting mold, after curing of monomeric material deposited in the casting mold, an ophthalmic device in the implementation of an intraocular lens is formed which comprises a lens and integrally formed-on haptics.

13. A method for manufacturing an intraocular lens, wherein the method comprises:

providing a casting mold, the casting mold comprising:

a first casting mold half with an optically accurately defined surface part, wherein the first casting mold half is manufactured with an injection mold comprising:

a first injection mold half in which an insert assembly is received, wherein the insert assembly comprises:

an insert assembly end surface, which bounds an injection mold cavity of the injection mold for forming the first casting mold half and which extends substantially perpendicular to an axial centerline of the insert assembly;

an outer part assembly which has an outer part assembly end surface which forms a part of the insert assembly end surface;

an inner part which has an optically accurately defined end surface which in a mounted condition is substantially adjacent the outer part assembly end surface and which forms a part of the insert assembly end surface; and at least one notch in the insert assembly end surface which forms a bounding structure cavity for forming a bounding structure which is an integral part of the first casting mold half to be formed with the injection mold, such that, in a condition of the first and the second casting mold halves placed onto each other, the bounding structure abuts against the second casting mold half and bounds at least one haptics cavity which links up with the lens cavity, wherein the haptics cavity is so configured that in use of the casting mold, after curing of monomeric material deposited in the casting mold, an ophthalmic device in the implementation of an intraocular lens is formed which comprises a lens and integrally formed-on haptics;

a second injection mold half which is movable relative to the first injection mold half from a closed to an opened position and vice versa; and a first injection mold cavity which is formed in the closed condition of the injection mold, which is at least partly bounded by the insert assembly end surface of the first insert assembly, and which is configured for manufacturing the first casting mold half; and a second casting mold half with an optically accurately defined surface part, wherein the first casting mold half and the second casting mold half in a condition placed onto each other bound a lens cavity, which lens cavity is at least partly bounded by said optically accurately defined surface parts, wherein the casting mold is provided with:

a bounding structure which is an integral part of the first casting mold half, such that in a condition of the first and the second casting mold half placed onto each other, the bounding structure abuts against the second casting mold half and bounds at least one haptics cavity which links up with the lens cavity, wherein the haptics cavity is so configured that in use of the casting mold, after curing of monomeric material deposited in the casting mold, an ophthalmic device in the implementation of an intraocular lens is formed which comprises a lens and integrally formed-on haptics;

injecting an amount of monomeric material into the first casting mold half;

placing the second casting mold half on the first casting mold half; and curing the monomeric material that is in the casting mold for forming in the casting mold an intraocular lens which comprises a lens and integrally formed-on haptics.

14. The insert assembly according to claim 2, wherein the at least one notch is so shaped as to form in the first casting mold half a bounding structure which comprises at least one upwardly projecting ridge, wherein the upwardly projecting ridge in cross section has a triangular shape with a sharp top.

15. The insert assembly according to claim 5, wherein intermediate part is provided with:

at least one additional intermediate part passage, wherein the at least one additional intermediate part passage forms an intermediate part passage opening in the end surface of the intermediate part which is bounded by intermediate part passage edges; and wherein the insert assembly comprises:

at least one intermediate part sub-element, associated with the at least one intermediate part passage, which in the direction of the axial centerline is slidably and fittingly receivable in the associated intermediate part passage, wherein the intermediate part sub-element has an end surface which is part of the outer part assembly end surface, wherein the end surface of the intermediate part sub-element is bounded by intermediate part sub-element circumferential edges, wherein the intermediate part passage edges and/or the intermediate part sub-element circumferential edges are chamfered, such that a notch triangular in cross section is obtained when the intermediate part sub-element is placed in the intermediate part, which triangular notch forms an additional upwardly projecting ridge of the first casting mold half for bounding a portion of the haptics cavity.

16. The insert assembly according to claim 5, provided with:

at least one keyway which is provided in an intermediate part circumferential wall extending in axial direction of the intermediate part, wherein the at least one keyway extends substantially perpendicular to the axial centerline;

a stop surface which is arranged in the outer part passage, wherein the stop surface is remote from the insert assembly end surface; and at least one key which is fittingly receivable in the associated at least one keyway, wherein in a mounted condition of the intermediate part in the outer part, the at least one key is received in the associated at least one keyway and abuts against the stop surface in the outer part passage, so that the intermediate part is positioned in axial direction relative to the outer part.

* * * * *